(12) United States Patent
Shoshtaev

(10) Patent No.: US 9,247,964 B1
(45) Date of Patent: Feb. 2, 2016

(54) SPINAL CROSS-CONNECTOR

(75) Inventor: Eugene Shoshtaev, San Diego, CA (US)

(73) Assignee: NUASIVE, INC., San Diego, CA (US)

( * ) Notice: Subject to any disclaimer, the term of this patent is extended or adjusted under 35 U.S.C. 154(b) by 175 days.

(21) Appl. No.: 13/410,218

(22) Filed: Mar. 1, 2012

Related U.S. Application Data

(60) Provisional application No. 61/447,702, filed on Mar. 1, 2011.

(51) Int. Cl.
*A61B 17/70* (2006.01)

(52) U.S. Cl.
CPC .............. *A61B 17/70* (2013.01); *A61B 17/7049* (2013.01); *A61B 17/7052* (2013.01)

(58) Field of Classification Search
CPC .............. A61B 17/70; A61B 17/7049–17/7052
USPC .................................................. 606/246–279
See application file for complete search history.

(56) References Cited

U.S. PATENT DOCUMENTS

| | | | |
|---|---|---|---|
| 4,361,141 A | 11/1982 | Tanner | |
| 4,569,338 A | 2/1986 | Edwards | |
| 4,641,636 A | 2/1987 | Cotrel | |
| 4,771,767 A | 9/1988 | Steffee | |
| 4,805,602 A | 2/1989 | Puno et al. | |
| 4,946,458 A | 8/1990 | Harms et al. | |
| 4,998,936 A | 3/1991 | Mehdian | |
| 5,005,562 A | 4/1991 | Cotrel | |
| 5,034,011 A | 7/1991 | Howland | |
| 5,042,982 A | 8/1991 | Harms et al. | |
| 5,084,049 A | 1/1992 | Asher et al. | |
| 5,092,866 A | 3/1992 | Breard et al. | |
| 5,092,867 A | 3/1992 | Harms et al. | |
| 5,092,893 A | 3/1992 | Smith | |
| 5,129,388 A | 7/1992 | Vignaud et al. | |
| 5,154,718 A | 10/1992 | Cozad et al. | |
| 5,176,680 A | 1/1993 | Vignaud et al. | |

(Continued)

FOREIGN PATENT DOCUMENTS

| | | |
|---|---|---|
| BR | PI0801130 | 6/2011 |
| DE | 3841008 | 6/1990 |

(Continued)

OTHER PUBLICATIONS

Beadling, "Harrington put the steel in spinal fixation",*Orthopedics Today*, (Jun. 2000).

(Continued)

*Primary Examiner* — Eduardo C Robert
*Assistant Examiner* — Michelle C. Eckman
(74) *Attorney, Agent, or Firm* — Jonathan Spangler; Jennifer Russell

(57) ABSTRACT

A spinal cross-connector comprises an elongated member, a first connector and a second connector. The first connector and the second connector are configured to receive spinal rods and adaptable to directly attach with pedicle screws. The first connector includes a first collet head, a first clamp and a first locking means. The second connector includes a second collet head, a second clamp and a second locking mans. The first locking means is configured to tighten over a first collet head and engage with the first connector. Similarly, the second locking means is configured to tighten over a second collet head and engage with the second connector. The engagement of the first locking means with the first connector and the second locking means with the second connector locks the spinal cross-connector.

20 Claims, 25 Drawing Sheets

(56) References Cited

U.S. PATENT DOCUMENTS

| | | | |
|---|---|---|---|
| 5,196,013 A | 3/1993 | Harms et al. |
| 5,207,678 A | 5/1993 | Harms et al. |
| 5,234,431 A | 8/1993 | Keller |
| 5,261,907 A | 11/1993 | Vagnaud et al. |
| 5,275,600 A | 1/1994 | Allard et al. |
| 5,312,405 A | 5/1994 | Korotko et al. |
| 5,330,473 A | 7/1994 | Howland |
| 5,375,823 A | 12/1994 | Navas |
| 5,387,213 A | 2/1995 | Breard et al. |
| 5,397,363 A | 3/1995 | Gelbard |
| 5,403,314 A | 4/1995 | Currier |
| 5,466,237 A | 11/1995 | Byrd, III et al. |
| 5,474,555 A | 12/1995 | Puno et al. |
| 5,478,340 A | 12/1995 | Kluger |
| 5,480,401 A | 1/1996 | Navas |
| 5,498,263 A | 3/1996 | Dinello et al. |
| 5,501,684 A | 3/1996 | Schlapfer et al. |
| 5,505,731 A | 4/1996 | Tornier |
| 5,522,816 A | 6/1996 | Dinello et al. |
| 5,536,268 A | 7/1996 | Griss |
| 5,540,688 A | 7/1996 | Navas |
| 5,545,163 A | 8/1996 | Miller et al. |
| 5,545,166 A | 8/1996 | Howland |
| 5,562,661 A | 10/1996 | Yoshimi et al. |
| 5,569,246 A | 10/1996 | Ojima et al. |
| 5,601,554 A | 2/1997 | Howland et al. |
| 5,607,425 A | 3/1997 | Rogozinski |
| 5,624,442 A | 4/1997 | Mellinger et al. |
| 5,630,816 A | 5/1997 | Kambin |
| 5,643,264 A | 7/1997 | Sherman et al. |
| 5,645,544 A | 7/1997 | Tai et al. |
| 5,665,122 A | 9/1997 | Kambin |
| 5,667,508 A | 9/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,676,665 A | 10/1997 | Bryan |
| 5,676,703 A | 10/1997 | Gelbard |
| 5,681,311 A | 10/1997 | Foley et al. |
| 5,688,272 A | 11/1997 | Montague et al. |
| 5,690,630 A | 11/1997 | Errico et al. |
| 5,693,053 A | 12/1997 | Estes |
| 5,702,393 A | 12/1997 | Pfaifer |
| 5,704,936 A | 1/1998 | Mazel |
| 5,716,355 A | 2/1998 | Jackson et al. |
| 5,725,527 A | 3/1998 | Biedermann et al. |
| 5,735,852 A | 4/1998 | Amrein et al. |
| 5,776,135 A | 7/1998 | Errico et al. |
| 5,800,435 A | 9/1998 | Errico et al. |
| 5,863,293 A | 1/1999 | Richelsoph |
| 5,873,878 A | 2/1999 | Harms et al. |
| 5,928,232 A | 7/1999 | Howland et al. |
| 5,928,237 A | 7/1999 | Farris et al. |
| 5,938,663 A | 8/1999 | Petreto |
| 5,944,719 A | 8/1999 | Leban |
| 5,944,720 A | 8/1999 | Lipton |
| 5,947,966 A | 9/1999 | Drewry et al. |
| 5,951,555 A | 9/1999 | Rehak et al. |
| 5,954,722 A | 9/1999 | Bono |
| 5,954,725 A | 9/1999 | Sherman et al. |
| 5,961,516 A | 10/1999 | Graf |
| 5,980,521 A | 11/1999 | Montague et al. |
| 5,980,523 A | 11/1999 | Jackson et al. |
| 6,004,322 A | 12/1999 | Bernstein |
| 6,030,389 A | 2/2000 | Wagner et al. |
| 6,063,089 A | 5/2000 | Errico et al. |
| 6,074,391 A | 6/2000 | Metz-Stavenhagen |
| 6,083,226 A | 7/2000 | Fiz |
| 6,113,600 A | 9/2000 | Drummond et al. |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,187,005 B1 | 2/2001 | Brace et al. |
| 6,190,388 B1 | 2/2001 | Michelson |
| 6,217,578 B1 | 4/2001 | Crozet et al. |
| 6,224,598 B1 | 5/2001 | Jackson |
| 6,234,705 B1 | 5/2001 | Troxell |
| 6,238,396 B1 | 5/2001 | Lombardo |
| 6,241,730 B1 | 6/2001 | Alby |
| 6,264,658 B1 | 7/2001 | Lee et al. |
| 6,267,765 B1 | 7/2001 | Taylor et al. |
| 6,273,914 B1 | 8/2001 | Papas |
| 6,280,445 B1 | 8/2001 | Morrison et al. |
| 6,283,967 B1 | 9/2001 | Troxell et al. |
| 6,296,644 B1 | 10/2001 | Saurat et al. |
| 6,306,137 B2 | 10/2001 | Troxell |
| 6,325,802 B1 | 12/2001 | Frigg |
| 6,328,740 B1 | 12/2001 | Richelsoph |
| 6,328,741 B1 | 12/2001 | Richelsoph |
| 6,379,354 B1 | 4/2002 | Rogozinski |
| 6,402,751 B1 | 6/2002 | Hoeck et al. |
| 6,413,258 B1 | 7/2002 | Bernhardt, Jr. |
| 6,482,207 B1 | 11/2002 | Errico |
| 6,485,491 B1 | 11/2002 | Farris et al. |
| 6,524,310 B1 | 2/2003 | Lombardo et al. |
| 6,554,832 B2 | 4/2003 | Shluzas |
| 6,602,253 B2 | 8/2003 | Richelsoph et al. |
| 6,616,668 B2 | 9/2003 | Altarac et al. |
| 6,626,904 B1 | 9/2003 | Jammet et al. |
| 6,641,583 B2 | 11/2003 | Shluzas et al. |
| 6,736,817 B2 | 5/2004 | Troxell et al. |
| 6,752,807 B2 | 6/2004 | Lin et al. |
| 6,761,721 B2 | 7/2004 | Burgess et al. |
| 6,783,526 B1 | 8/2004 | Lin et al. |
| 6,872,208 B1 | 3/2005 | McBride et al. |
| 6,875,211 B2 | 4/2005 | Nichols et al. |
| 6,887,241 B1 | 5/2005 | McBride et al. |
| 6,899,714 B2 | 5/2005 | Vaughan |
| 6,916,319 B2 * | 7/2005 | Munting .................. 606/278 |
| 6,958,066 B2 | 10/2005 | Richelsoph et al. |
| 6,960,212 B2 | 11/2005 | Richelsoph et al. |
| 7,029,474 B2 | 4/2006 | Richelsoph et al. |
| 7,066,938 B2 | 6/2006 | Slivka et al. |
| 7,083,622 B2 | 8/2006 | Simonson |
| 7,104,993 B2 | 9/2006 | Baynham et al. |
| 7,122,036 B2 | 10/2006 | Vanacker |
| 7,137,986 B2 | 11/2006 | Troxell et al. |
| 7,160,301 B2 | 1/2007 | Cordaro |
| 7,406,775 B2 | 8/2008 | Funk et al. |
| 7,678,112 B2 | 3/2010 | Rezach |
| 8,062,339 B2 | 11/2011 | Hammer et al. |
| 2001/0034521 A1 | 10/2001 | Bailey et al. |
| 2002/0007183 A1 * | 1/2002 | Lee et al. .................. 606/61 |
| 2002/0052603 A1 | 5/2002 | Nichols et al. |
| 2002/0143330 A1 | 10/2002 | Shluzas |
| 2002/0169448 A1 | 11/2002 | Vanacker |
| 2003/0023244 A1 | 1/2003 | Richelsoph et al. |
| 2003/0028191 A1 | 2/2003 | Shluzas |
| 2003/0045874 A1 * | 3/2003 | Thomas, Jr. .............. 606/61 |
| 2003/0045878 A1 | 3/2003 | Petit et al. |
| 2003/0060823 A1 | 3/2003 | Bryan |
| 2003/0149432 A1 | 8/2003 | Frigg et al. |
| 2003/0153917 A1 | 8/2003 | Richelsoph et al. |
| 2003/0163133 A1 | 8/2003 | Altarac et al. |
| 2003/0212398 A1 | 11/2003 | Jackson |
| 2004/0116928 A1 | 6/2004 | Young et al. |
| 2004/0138662 A1 | 7/2004 | Landry et al. |
| 2004/0147928 A1 | 7/2004 | Landry et al. |
| 2004/0260287 A1 | 12/2004 | Ferree |
| 2005/0010217 A1 | 1/2005 | Dalton |
| 2005/0070901 A1 | 3/2005 | David |
| 2005/0080416 A1 * | 4/2005 | Ryan et al. ............... 606/61 |
| 2005/0090821 A1 | 4/2005 | Berrevoets et al. |
| 2005/0192572 A1 | 9/2005 | Abdelgany et al. |
| 2005/0228326 A1 | 10/2005 | Kalfas et al. |
| 2005/0228382 A1 | 10/2005 | Richelsoph et al. |
| 2005/0277923 A1 | 12/2005 | Sweeney |
| 2005/0288670 A1 | 12/2005 | Panjabi et al. |
| 2006/0036252 A1 | 2/2006 | Baynham et al. |
| 2006/0052783 A1 | 3/2006 | Dant et al. |
| 2006/0052786 A1 | 3/2006 | Dant et al. |
| 2006/0058789 A1 | 3/2006 | Kim et al. |
| 2006/0064091 A1 | 3/2006 | Ludwig et al. |

(56) References Cited

U.S. PATENT DOCUMENTS

| | | |
|---|---|---|
| 2006/0064093 A1 | 3/2006 | Thramann et al. |
| 2006/0149229 A1 | 7/2006 | Kwak et al. |
| 2006/0217718 A1 | 9/2006 | Chervitz et al. |
| 2006/0229606 A1 | 10/2006 | Clement et al. |
| 2006/0235393 A1 | 10/2006 | Bono et al. |
| 2006/0241596 A1 | 10/2006 | Rezach |
| 2006/0247624 A1 | 11/2006 | Banouskou et al. |
| 2006/0264933 A1 | 11/2006 | Baker et al. |
| 2006/0271045 A1 | 11/2006 | Hubbard et al. |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2007/0049932 A1 | 3/2007 | Richelsoph et al. |
| 2007/0055239 A1 | 3/2007 | Sweeney et al. |
| 2007/0083201 A1 | 4/2007 | Jones et al. |
| 2007/0149973 A1 | 6/2007 | Clement et al. |
| 2007/0173829 A1 | 7/2007 | Drewry et al. |
| 2007/0173833 A1 | 7/2007 | Butler et al. |
| 2007/0213721 A1 | 9/2007 | Markworth et al. |
| 2007/0213723 A1 | 9/2007 | Markworth et al. |
| 2007/0233062 A1 | 10/2007 | Berry |
| 2007/0233090 A1 | 10/2007 | Naifeh |
| 2007/0233119 A1 | 10/2007 | Markworth |
| 2007/0270808 A1 | 11/2007 | Drewry et al. |
| 2007/0270809 A1 | 11/2007 | Drewry et al. |
| 2007/0288009 A1 | 12/2007 | Brown et al. |
| 2008/0021464 A1 | 1/2008 | Morin et al. |
| 2008/0051780 A1 | 2/2008 | Vaidya et al. |
| 2008/0071273 A1 | 3/2008 | Hawkes et al. |
| 2008/0091204 A1 | 4/2008 | Kuiper et al. |
| 2008/0109039 A1 | 5/2008 | Michielli et al. |
| 2008/0140075 A1 | 6/2008 | Ensign et al. |
| 2008/0172093 A1 | 7/2008 | Nilsson |
| 2008/0177315 A1 | 7/2008 | Usher |
| 2008/0177323 A1 | 7/2008 | Null et al. |
| 2008/0255617 A1 | 10/2008 | Cho et al. |
| 2008/0269742 A1 | 10/2008 | Levy et al. |
| 2008/0306534 A1 | 12/2008 | Winslow et al. |
| 2008/0306535 A1 | 12/2008 | Winslow et al. |
| 2008/0312692 A1 | 12/2008 | Brennan et al. |
| 2009/0043338 A1 | 2/2009 | Laager et al. |
| 2009/0062860 A1 | 3/2009 | Frasier et al. |
| 2009/0125065 A1 | 5/2009 | Laager et al. |
| 2009/0216277 A1 | 8/2009 | Tornier et al. |
| 2009/0264931 A1* | 10/2009 | Miller et al. ................ 606/251 |
| 2009/0318968 A1 | 12/2009 | Duggal et al. |
| 2010/0094345 A1* | 4/2010 | Saidha et al. ................ 606/250 |
| 2010/0094346 A1 | 4/2010 | Matityahu |
| 2010/0094349 A1 | 4/2010 | Hammer et al. |
| 2010/0160981 A1 | 6/2010 | Butler et al. |
| 2010/0191289 A1 | 7/2010 | Ludwig et al. |
| 2010/0198260 A1 | 8/2010 | Gabelberger et al. |
| 2010/0204733 A1 | 8/2010 | Rathbun et al. |
| 2010/0211100 A1 | 8/2010 | Mack |
| 2010/0268279 A1 | 10/2010 | Gabelberger et al. |
| 2010/0324599 A1 | 12/2010 | Montello et al. |
| 2011/0034957 A1 | 2/2011 | Biedermann |
| 2011/0046675 A1 | 2/2011 | Barrus et al. |
| 2011/0071569 A1 | 3/2011 | Black |
| 2011/0106178 A1 | 5/2011 | Schwab |
| 2011/0184462 A1 | 7/2011 | Gil et al. |
| 2012/0029566 A1 | 2/2012 | Rezach |
| 2012/0071926 A1 | 3/2012 | Jani et al. |
| 2012/0101529 A1 | 4/2012 | Ludwig et al. |
| 2012/0130436 A1 | 5/2012 | Haskins et al. |
| 2012/0226316 A1* | 9/2012 | Dant et al. ................ 606/250 |
| 2013/0023932 A1* | 1/2013 | Helgerson ................ 606/247 |

FOREIGN PATENT DOCUMENTS

| | | |
|---|---|---|
| DE | 9004960 | 8/1992 |
| EP | 0283373 | 9/1988 |
| EP | 1743585 | 1/2007 |
| FR | 2624720 | 6/1989 |
| WO | WO 95/13754 | 5/1995 |
| WO | WO 2006/025919 | 3/2006 |
| WO | WO 2007/130007 | 11/2007 |
| WO | WO 2010/045219 | 4/2010 |
| WO | WO 2011/057178 | 5/2011 |

OTHER PUBLICATIONS

Dipreta, "The Iliac Nail/Screw in a Modified Galveston Technique for Sacropelvic Fixation", *Am. Acad. of Ortho. Surg., 67th mtg., PE184*, (Mar. 19, 2000).

Ebrahim, "Posterior Lateral Mass Screw Fixation: Anatomic and Radiographic Considerations", *U.P.O.J.* vol. 12 (Spring 1999), 66-72.

Erickson, "Biomechanical Assessment of Conventional Unit Rod Fixation Versus a Unit Rod Pedicle Screw Construct", *Spine*, vol. 29, No. 12, (2004), 1314-1319.

Pham, "Upper cervical spine surgery in rheumatoid arthritis: retrospective study of 30 patients followed for two years or more after Cotrel-Dubousset instrumentation", *Joint Bone Spine*, 67 (2000), 434-440.

Sanders, "Treating, managing spinal deformity in young patients", Orthopedics Today (Jul. 2001).

Spiegel, "Anterior instrumentation in the Treatment of Scolisosis" *U.P.O.J.*, vol. 11, (Spring 1998), 19-26.

Wood, "Torsional Rigidity of Scoliosis Constructs", *Spine*, vol. 25, No. 15, (2000), 1893-1898.

\* cited by examiner

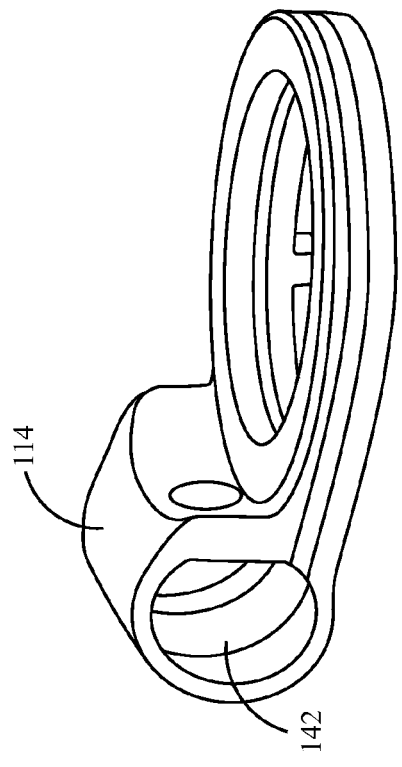
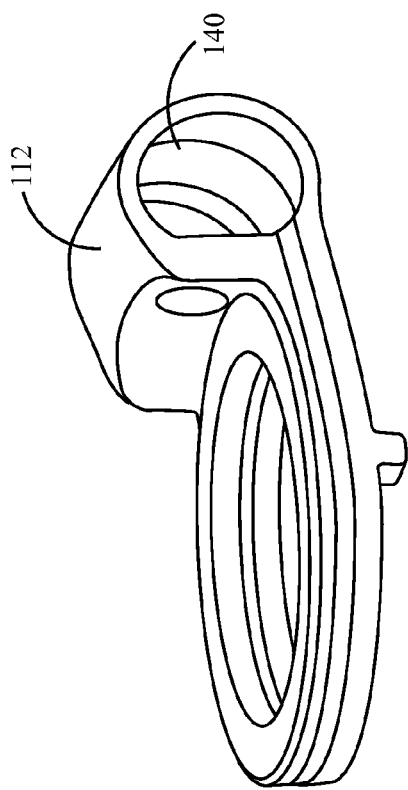
FIG. 4A
FIG. 4B

SPINAL CROSS-CONNECTOR

CROSS-REFERENCE TO RELATED APPLICATIONS

This application claims the benefit of the filing date of U.S. Provisional Application No. 61/447,702, which was filed on Mar. 1, 2011. The entire contents of U.S. Provisional Application No. 61/447,702 is incorporated herein by reference.

I. TECHNICAL FIELD

This embodiment relates to spinal cross-connectors, and more specifically to an easily implantable spinal cross-connector that possesses a simple and sturdy locking mechanism for securing spinal fixation rods on vertebrae.

II. BACKGROUND

Various spinal fixation devices have been developed in the art. The spinal fixation rods are spinal fixation devices configured to fix adjacent vertebrae of a spine relative to each other. The spinal fixation rods are used in orthopedic surgeries to repair spinal abnormalities. The spinal rods are configured to attach with the vertebrae using anchoring devices like pedicle screws, bolts and hooks. Patients experience extreme and debilitating pain because of spinal column disorders like, spondylolisthesis and scoliosis. A treatment technique called spinal fixation effectively treats these disorders utilizing spinal fixation rods that mechanically immobilize areas of the spine causing the eventual fusion of the treated vertebrae.

After prolonged use, the spinal fixation rods may twist and may cause the rods to bend. To resist the twisting movements, a number of spinal cross-connectors are inserted between the spinal fixation rods. However, existing cross-connectors suffer from a number of limitations. For example, conventional cross-connectors require extra coupling devices for support. Theses coupling devices cause stress to the cross-connectors that will cause fixation devices to bend.

SUMMARY

One embodiment of a spinal cross-connector comprises an elongated member, a first connector and a second connector. The first connector is configured to receive a first spinal rod and adaptable to directly attach with a first pedicle screw. The first connector includes a first collet head having a recess to receive a first tulip and a plurality of cutouts to accommodate the first spinal rod. The second connector is configured to receive a second spinal rod and directly attach with a second pedicle screw. The second connector includes a second collet head having a recess to receive a second tulip and a plurality of cutouts to accommodate the second spinal rod.

The elongated member has a first end and a second end. The first end of the elongated member is surrounded by a first ball spring collar and the second end of the elongated member is surrounded by a second ball spring collar. The elongated member is configured to translate through the first ball spring collar and the second ball spring collar to adjust to the distance between the first spinal rod and the second spinal rod. The first clamp includes a first spherical pocket and the second clamp includes a second spherical pocket. The first spherical pocket is configured to receive the first ball spring collar of the elongated member and permits adjustment of the elongated member relative to the first clamp. And the second spherical pocket is configured to receive the second ball spring collar of the elongated member and permits adjustment of the elongated member relative to the second clamp. The first ball spring collar and the second ball spring collar are configured to rotate in the first spherical pocket and the second spherical pocket respectively to allow an axial adjustment.

Preferably, the first locking means is configured to tighten over the first collet head and engage with the first connector. Upon engaging with the first connector, the first locking means locks the first clamp with the first end of the elongated member and also locks the first connector with the first tulip. In the same way, the second locking means is tightened over the second collet head. The second locking means is configured to engage with the second connector for locking the second clamp with the second end and also for locking the second connector with the second tulip. The engagement of the first locking means with the first connector and the second locking means with the second connector locks the spinal cross-connector. This locking mechanism does not require any additional locking step above the spinal canal thereby making its implantation faster. When the spinal cross-connector gets locked, it firmly secures and provides additional stability to the spinal rods, engaged with the collet heads. The first connector and the second connector include a first central opening and a second central opening respectively.

Another embodiment of a spinal cross-connector also has an elongated member, a first connector and a second connector. The elongated member includes a first end and a second end. The first connector includes a first collet head configured to receive a first tulip and accommodate the first spinal rod. Similarly, the second connector includes a second collet head configured to receive a second tulip and adaptable to accommodate the second spinal rod. The first connector and the second connector are configured to receive spinal rods, and directly attach with pedicle screws. The elongated member includes a flat portion that allows preventing the elongated member from turning to 360 degrees thereby restricting the range of motion to a useful range.

The first clamp and the second clamp allow the elongated member to translate for adjusting to the distance between the spinal rods. The first locking means and the second locking means are tightened over the first collet head and the second collet head respectively. Upon tightening, first and second connectors get locked with the first and second tulips, and the first and the second clamps get locked with the first and second ends of the elongated member respectively.

The elongated member is substantially L-shaped. The L-shaped elongated member includes a straight side and a curved side. The straight side allows the elongated member to translate through the first clamp and the second clamp for adjusting to the distance between the spinal rods. The curved side is configured to rotate axially to permit diverging angles between the first tulip and the second tulip.

Yet another embodiment of a spinal cross-connector of the present invention is similar to the first embodiment discussed above, but, the second collect head includes a collapsible spherical pocket configured to receive a ball end attached at the second end of the elongated member. The collapsible spherical pocket and the ball end are configured to permit angular adjustments of the elongated member. The first end of the elongated member is straight and allows the elongated member to translate through the first clamp of the first connector and adjust to the distance between the spinal rods. The second collet head is configured to snap onto the second tulip and locks the second tulip. Once the second locking means is tightened over the second collet head, the collapsible spherical pocket collapse on the ball end of the elongated member and prevents further movement. This locking mechanism allows the spinal rods to firmly secure in the vertebrae.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

FIG. 4A is a perspective view of the first clamp of the present invention;

FIG. 4B is a perspective view of second clamp of the present invention;

DETAILED DESCRIPTION

Illustrative embodiments of the cross-connector are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

The present description illustrates a spinal cross-connector to provide stability and rigidity to spinal rods. The spinal cross-connectors are implanted in vertebra using bone anchoring elements, for example, pedicle screws and/or hooks. The spinal cross-connectors and the bone anchoring elements hold the spinal rods in a desired position.

Figure 1:
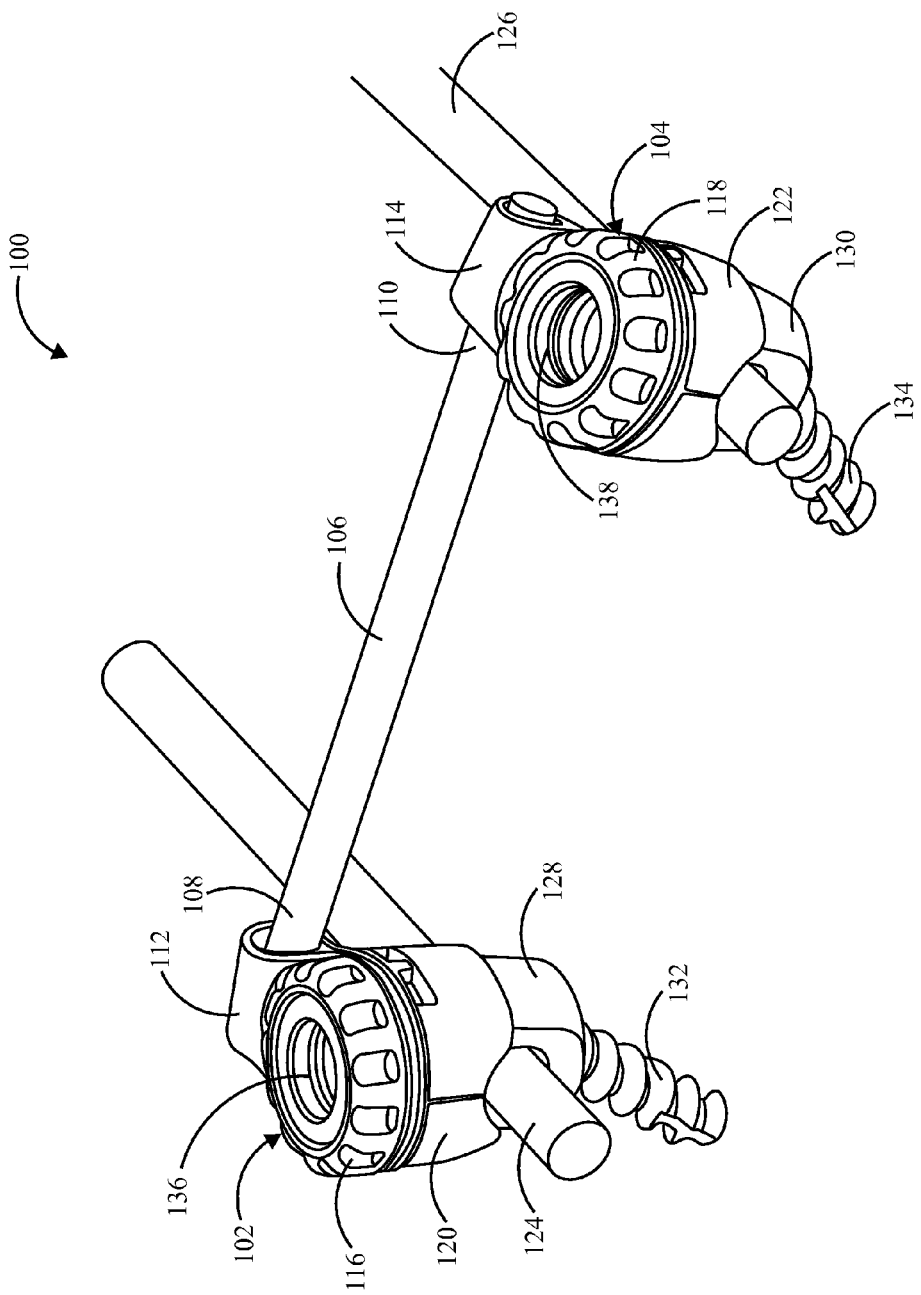
FIG. 1 is a perspective view of a spinal cross-connector of the present invention.
Figure 2:
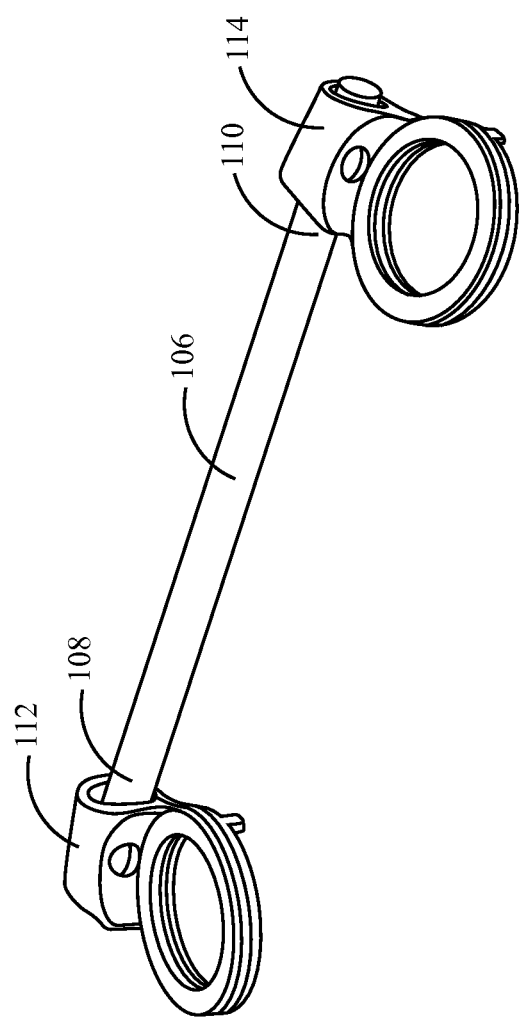
FIG. 2 is a perspective view of an elongated member attached with a clamp of the present invention.

Referring now to FIGS. 1 and 2, an embodiment of a spinal cross-connector 100 configured to provide stability and rigidity to a plurality of bilateral spinal rods 124, 126 is illustrated. The spinal cross-connector 100 comprises an elongated member 106, a first connector 102 and a second connector 104. The elongated member 106 includes a first end 108 and a second end 110. The first connector 102 is configured to receive a first spinal rod 124 and directly attach with a first pedicle screw 132. The first connector 102 includes a first collet head 120 having a recess to receive a tulip head 128 of the first pedicle screw and a plurality of cutouts to accommodate the first spinal rod 124. Similarly, the second connector 104 is configured to receive a second spinal rod 126 and adaptable to directly attach with a second pedicle screw 134. The second connector 104 further includes a second collet head 122 having a recess to receive a tulip head 130 of the second pedicle screw and a plurality of cutouts to accommodate the second spinal rod 126.

Figure 3:
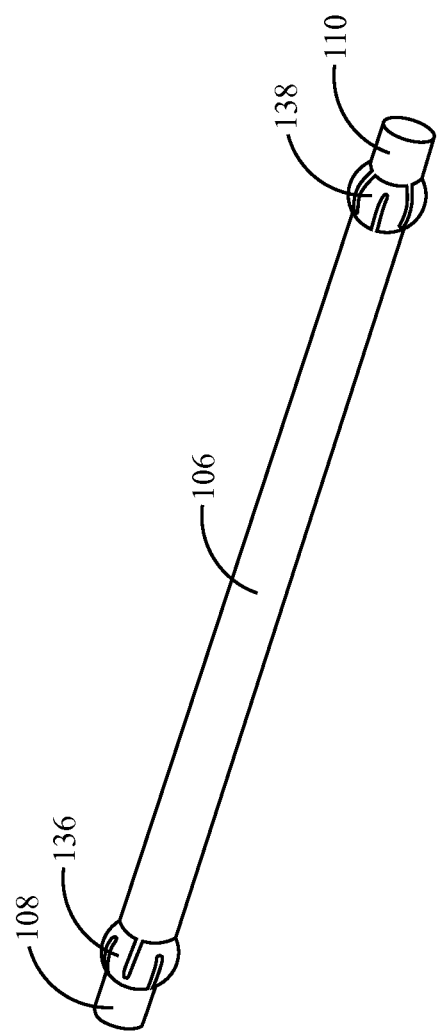
FIG. 3 is a perspective view of the elongated member having a first ball spring collar and a second ball spring collar surrounded at a first end and a second end of the present invention.

As shown in FIG. 3, the first end 108 of the elongated member 106 is surrounded by a first ball spring collar 136 and the second end 110 of the elongated member 106 is surrounded by a second ball spring collar 138. The elongated member 106 is configured to translate through the first ball spring collar 136 and the second ball spring collar 138 to adjust to the distance between the first spinal rod 124 and the second spinal rod 126. The first ball spring collar 136 and the second ball spring collar 138 allow rotational adjustment to the first and second connectors 102, 104 in an axial plane to provide stability to the spinal cross-connector 100 when the first tulip 128 is positioned deeper than the second tulip 130 on the vertebra.

According to FIGS. 4A and 4B, the first clamp 112 includes a first spherical pocket 140 and the second clamp 114 includes a second spherical pocket 142. The first spherical pocket 140 is configured to receive the first ball spring collar 136 of the elongated member 106 and permits adjustment of the elongated member 106 relative to the first clamp 112. Similarly, the second spherical pocket 142 is configured to receive the second ball spring collar 138 of the elongated member 106 and permits adjustment of the elongated member 106 relative to the second clamp 114. The first ball spring collar 136 and the second ball spring collar 138 are configured to rotate in the first spherical pocket 140 and the second spherical pocket 142 respectively to allow an axial adjustment.

Preferably, the first locking means 116 is configured to tighten over the first collet head 120 and engage with the first connector 102. Upon engaging with the first connector 102, the first locking means 116 locks the first clamp 112 with the first end 108 of the elongated member 106 and also locks the first connector 102 with the first tulip 128. Therefore, with two simple locking steps the first connector 102 gets tightly locked. In the same way, the second locking means 118 is tightened over the second collet head 122. Similarly, the second locking means 118 is configured to engage with the second connector 104 for locking the second clamp 114 with the second end 110 of the elongated member 106 and also for locking the second connector 104 with the second tulip 130. The engagement of the first locking means 116 with the first connector 102 and the second locking means 118 with the second connector 104 locks the spinal cross-connector 100. This locking mechanism does not require any additional locking step above the spinal canal thereby making its implantation faster. When the spinal cross-connector 100 gets locked, it firmly secures and provides additional stability to the spinal rods 124, 126 engaged with the collet heads 120, 122. The first connector 102 and the second connector 104 include a first central opening 136 and a second central opening 138 respectively.

Figure 5:
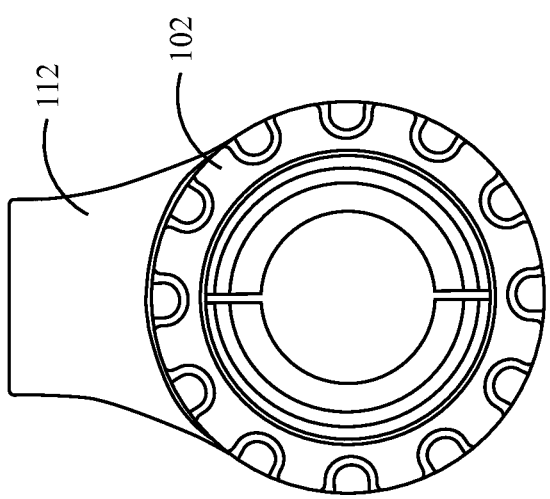
FIG. 5 is a top view of the first connector engaged with the first clamp of the present invention.

As shown in FIG. 5, a top view of the first connector 102 engaged with the first clamp 112 is illustrated. The elongated member 106 translates through the first spherical pocket 140 of the first clamp 112 and second spherical pocket 142 through a conical passage. The conical passage is larger than the diameter of the elongated member 106 that allows the elongated member 106 to translate freely through the spherical pockets 140 and 142.

In use, the shank of the first pedicle screw 132 engaged with the tulip head 128 of the first pedicle screw is inserted into a first vertebrae. Then the shank of the second pedicle screw 134 engaged with the tulip head 130 of the second pedicle screw is inserted into a second vertebrae. The first spinal rod 124 is translated through the first pedicle screw 132 and the second spinal rod 126 is translated through the second pedicle screw 134. Next, the first collet head 120 is placed over the first spinal rod 124 and a second collet head 122 is placed over the second spinal rod 126. The elongated member 106 is engaged with the first clamp 112 and the second clamp 114. The first clamp 112 is inserted into the first collet head 120 and the second clamp 114 is inserted on the second collet head 122. The first connector 102 is locked by tightening the first locking means 116 with the first collet head 120 and the second connector 104 is locked by tightening the second locking means 118 with the second collet head 122. The locking of the first connector 102 and the second connector 104 causes locking of the spinal cross-connector 100.

Figure 6:
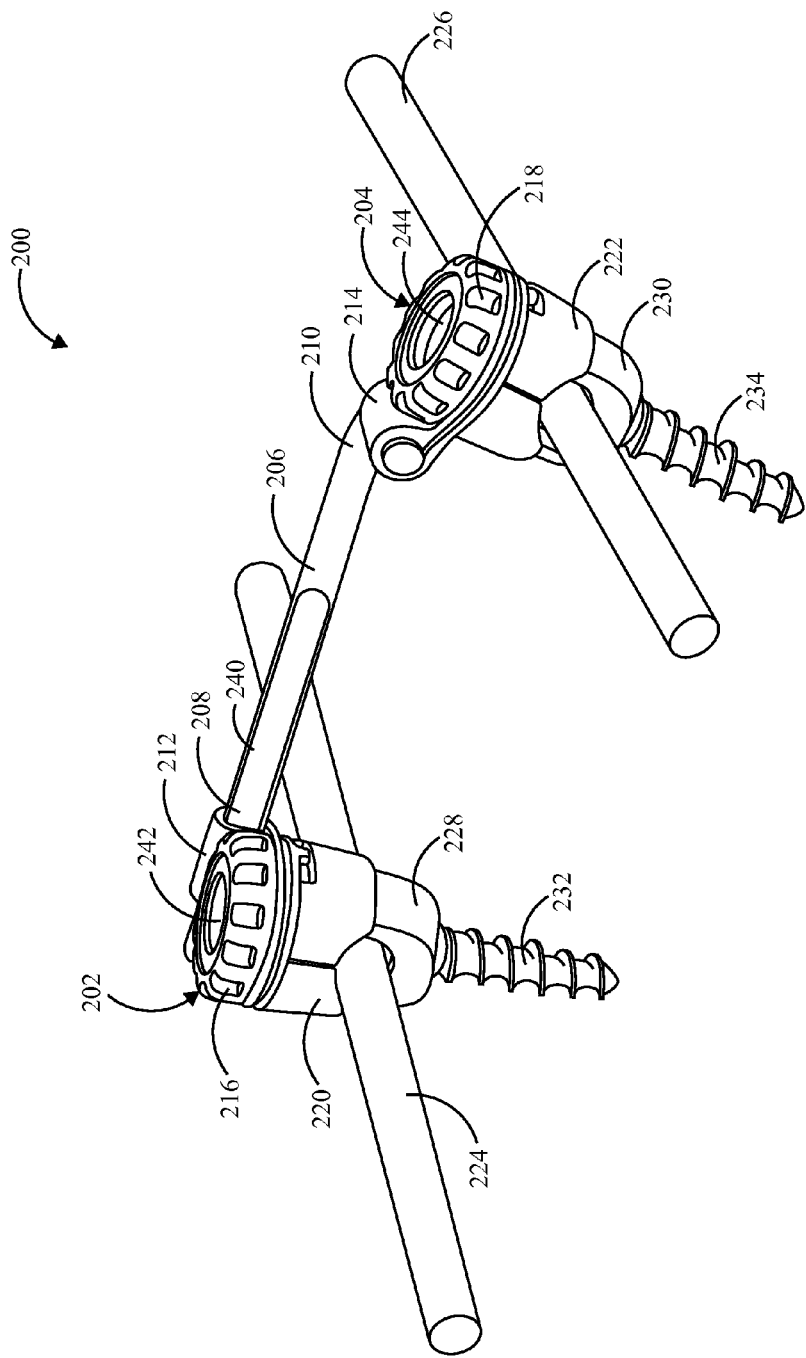
FIG. 6 is a perspective view of another embodiment of a spinal cross-connector of the present invention.
Figure 7:
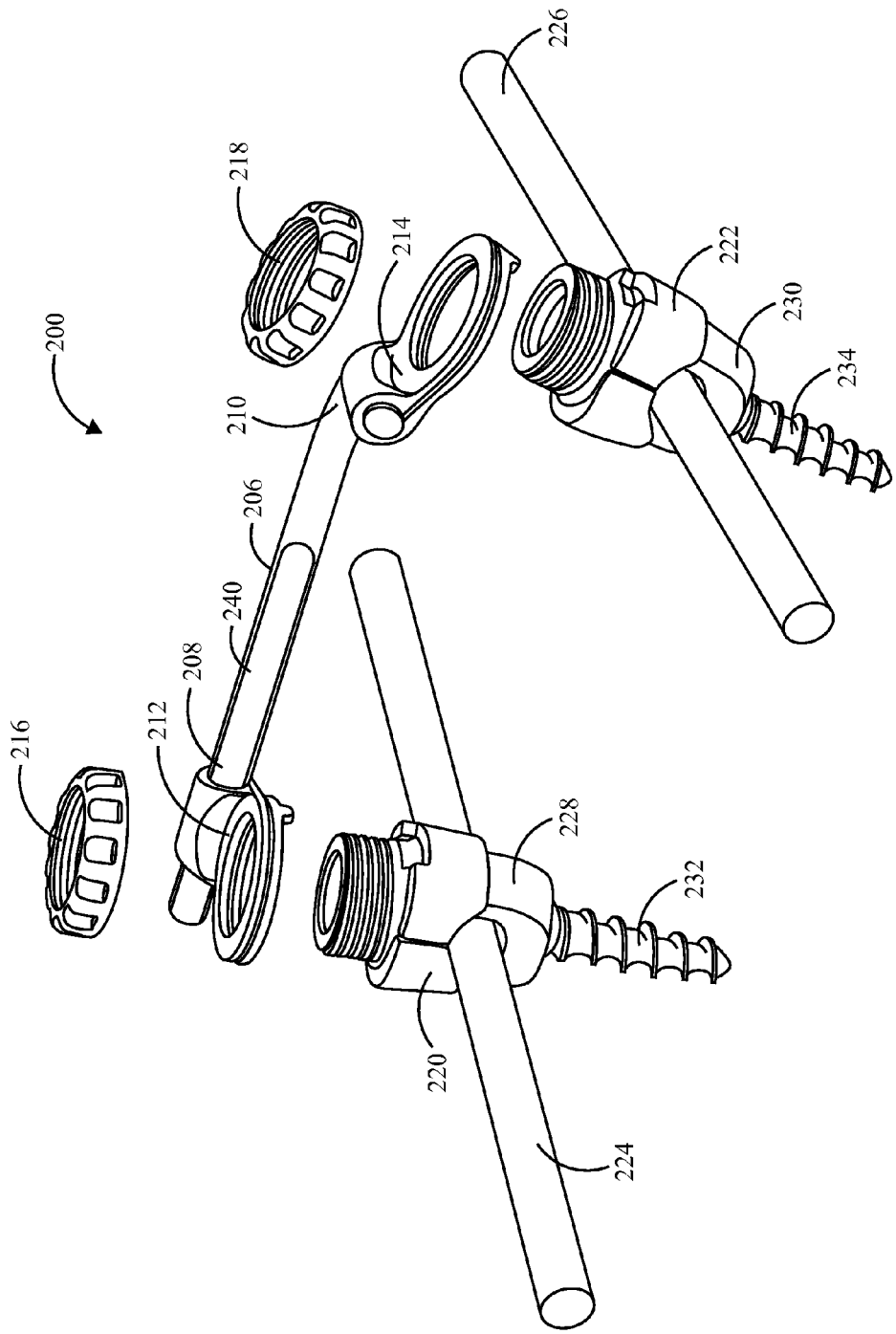
FIG. 7 is an exploded view of the spinal cross-connector shown in FIG. 6.
Figure 8:
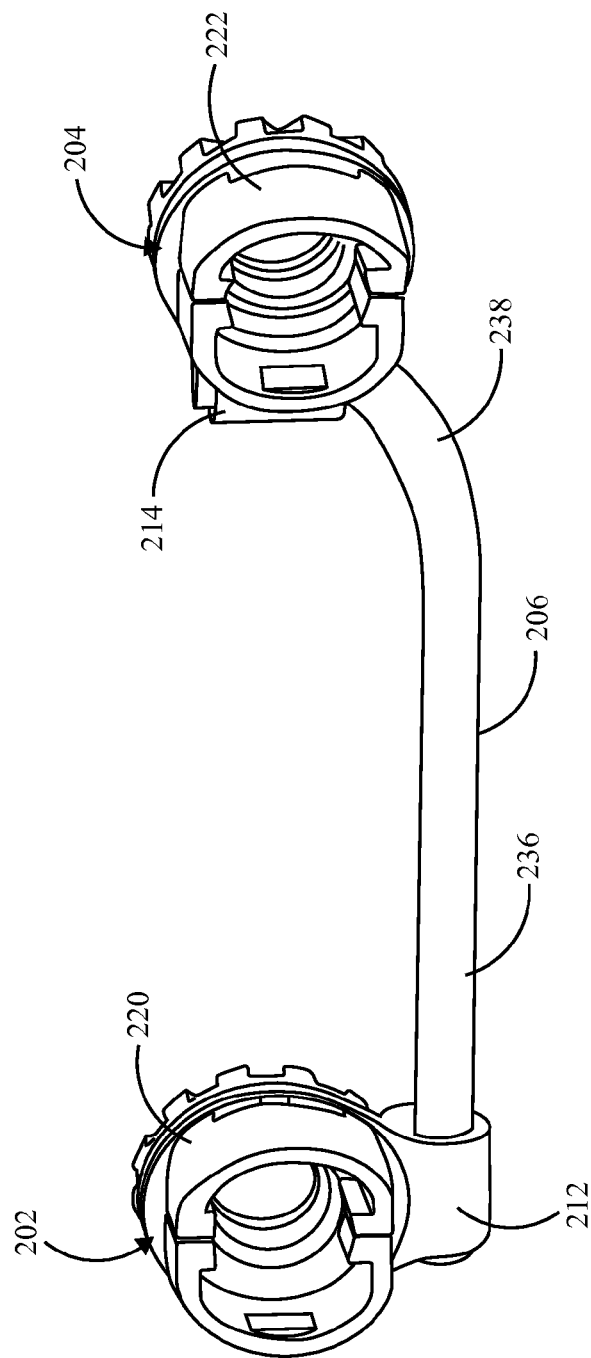
FIG. 8 is a perspective view of a pair of connectors and an elongated member of the spinal cross-connector shown in FIG. 6.

Referring now to FIGS. 6-8, another embodiment of a spinal cross-connector 200 is illustrated. The spinal cross-connector 200 in this embodiment is similar to that of the embodiment described in FIG. 1, except that the elongated member and the clamps have some structural difference. Elements in this second embodiment that are similar to those in the first embodiment are referenced with like numbers, but in the two hundreds rather than the one hundreds. Accordingly, the spinal cross-connector 200 in this embodiment comprises an elongated member 206, a first connector 202 and a second connector 204. The elongated member 206 includes a first end 208 and a second end 210. The first connector 202 includes a first collet head 220 configured to receive a first tulip 228 and to accommodate the first spinal rod 224. Similarly, the second connector 204 includes a second collet head 222 configured to receive a second tulip 230 and to accommodate the second spinal rod 226. The first connector 202 and the second connector 204 are configured to receive the spinal rods 224 and 226 and directly attach with pedicle screws 232, 234 respectively. The elongated member 206 includes a flat portion 240 that allows preventing the elongated member 206 from turning to 360 degrees thereby restricting the range of motion to a useful range.

Referring to FIG. 7, the first clamp 212 and the second clamp 214 allow the elongated member 206 to translate for adjusting to the distance between the spinal rods 224 and 226. The first and second clamps 212, 214 get depressed by the first and second locking means 216 and 218 to lock the elongated member 206 in place.

The first locking means 216 and the second locking means 218 are similar to the locking means 116, 118 described in FIG. 1. The first locking means 216 and the second locking means 218 are tightened over the first collet head 220 and the second collet head 222 respectively. Upon tightening, first and second connectors 202, 204 get locked with the first and second tulips 228, 230 and the first and the second clamps 212, 214 get locked with the first and second ends 208, 210 of the elongated member 206 respectively.

Preferably, as shown in FIG. 8, the elongated member 206 is substantially L-shaped. The L-shaped elongated member 206 includes a straight side 236 and a curved side 238. The straight side 236 allows the elongated member 206 to translate through the first clamp 212 and the second clamp 214 for adjusting to the distance between the spinal rods 224 and 226. The curved side 238 is configured to rotate axially to permit diverging angles between the first tulip 228 and the second tulip 230. The collet heads 220 and 222 are configured to snap onto the tulips 228 and 230 and later be locked to the tulips 228 and 230.

Figure 9:
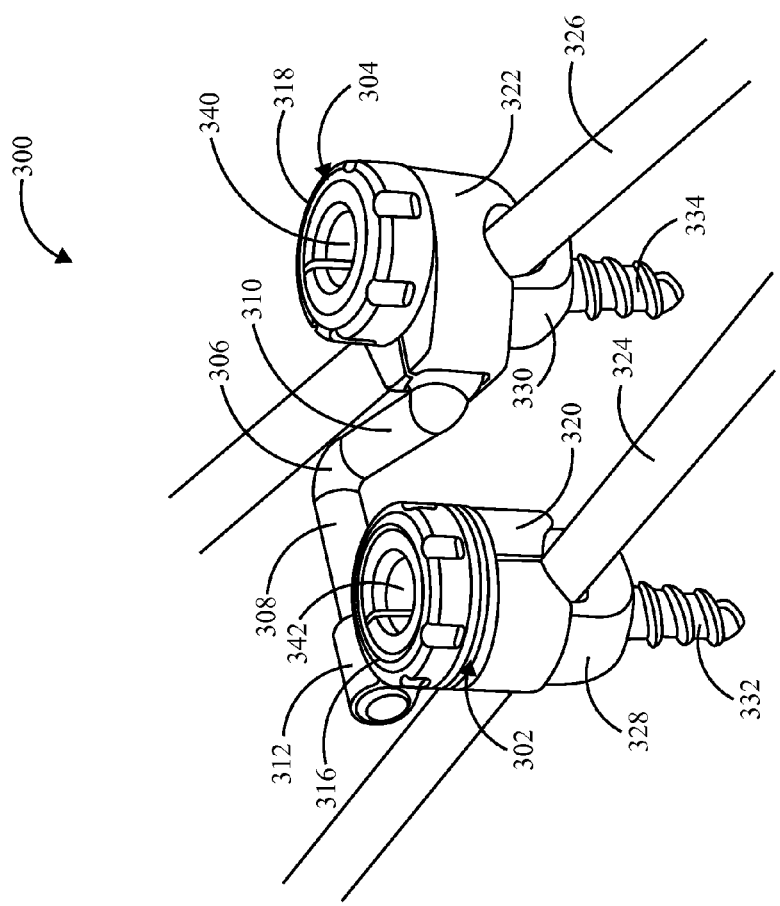
FIG. 9 is a perspective view of yet another embodiment of a spinal cross-connector of the present invention.
Figure 10:
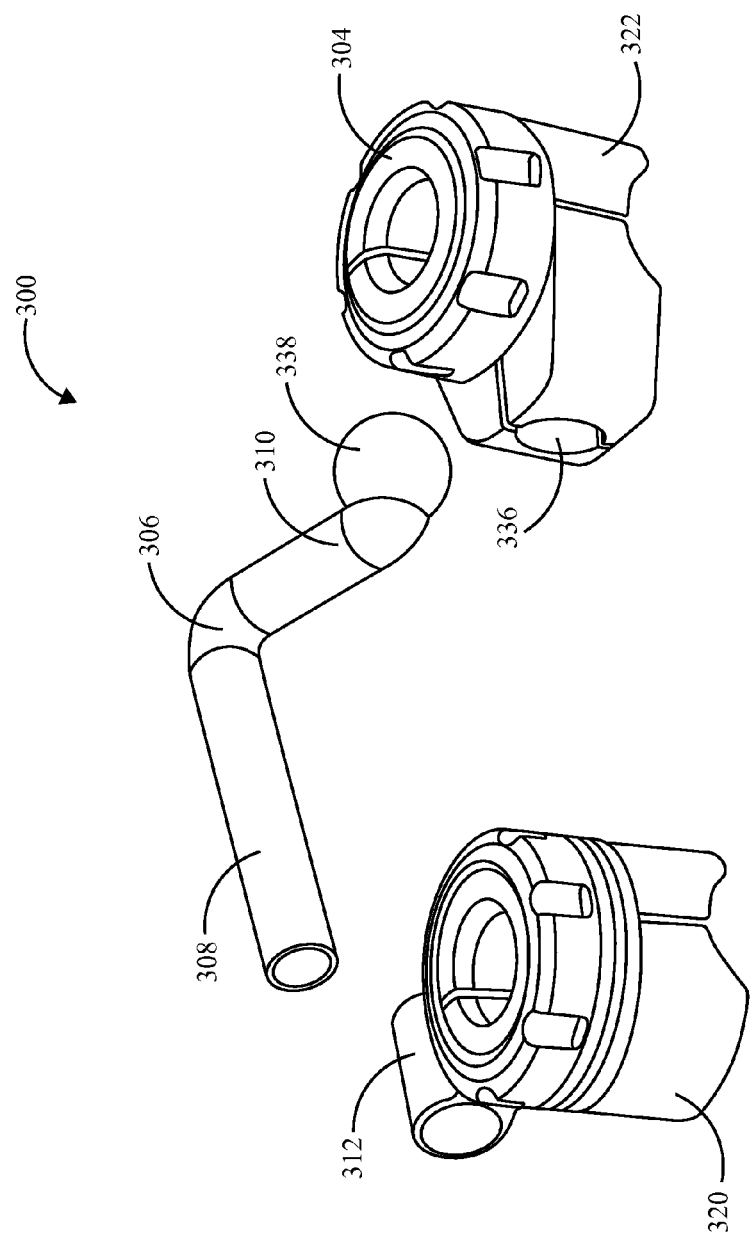
FIG. 10 is an exploded view of a pair of connectors attached with an elongated member of the spinal cross-connector shown in FIG. 9.
Figure 11:
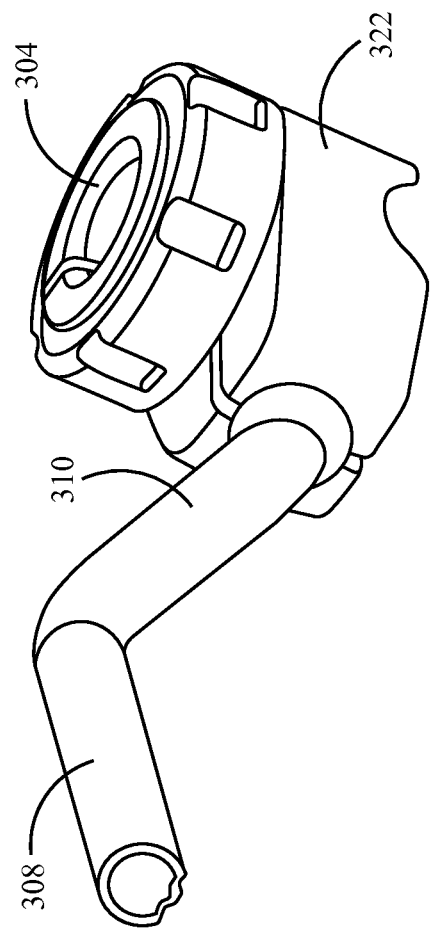
FIG. 11 is a perspective view of a second connector and an elongated member as shown in FIG. 9.

Referring now to FIGS. 9-11, yet another embodiment of a spinal cross-connector 200 is illustrated. The spinal cross-connector 300 in this embodiment is similar to that of the embodiment described in FIGS. 6-8, except that the second connector 304 is modified and includes a modified second collet head 322 and a second locking means 318. Elements in this second embodiment that are similar to those in the first embodiment are referenced with like numbers, but in the three hundreds rather than the two hundreds. Accordingly, as shown in FIG. 9, the spinal cross-connector 300 in this embodiment comprises an elongated member 306, a first connector 302 and a second connector 304. The elongated member 306 includes a first end 308 and a second end 310. The first connector 302 includes a first collet head 320 having a recess to receive a first tulip 328 and a plurality of cutouts to accommodate the first spinal rod 324. Similarly, the second connector 304 includes a second collet head 322 having a recess to receive a second tulip 330 and a plurality of cutouts to accommodate the second spinal rod 326. The first connector 302 and the second connector 304 are configured to receive spinal rods 324, 326 and directly attaches with the pedicle screws 332 and 334. The first connector 302 and the second connector 304 include a first central opening 342 and a second central opening 340 respectively.

Preferably, as shown in FIG. 10, the second collect head 322 includes a collapsible spherical pocket 336 configured to receive a ball end 338 attached at the second end 310 of the elongated member 306. The collapsible spherical pocket 336 and the ball end 338 are configured to permit angular adjustments of the elongated member 306. The first end 308 of the elongated member 306 is straight and allows the elongated member 306 to translate through the first clamp 312 of the first connector 302 and adjust to the distance between the spinal rods 324, 326.

Referring to FIG. 11, the second collet head 322 is configured to snap onto the first tulip 328 and locks the second tulip 330. Preferably, when the second locking means 318 is tightened over the second collet head 322, the collapsible spherical pocket 336 collapses on the ball end 338 of the elongated member 306 and prevents further movement. This locking mechanism allows the spinal rods 324, 326 to firmly secure in the vertebrae.

Figure 12:
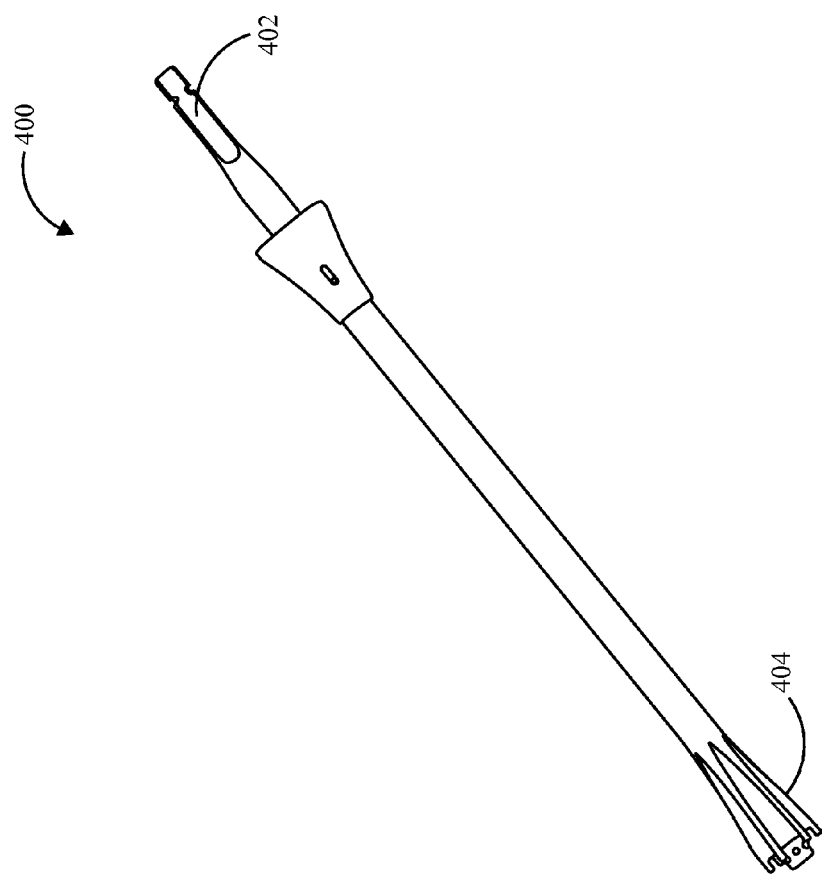
FIG. 12 is a perspective view of a handle connector and a distal end of a driver configured to use with the first connector and the second connector of the present invention.
Figure 13:
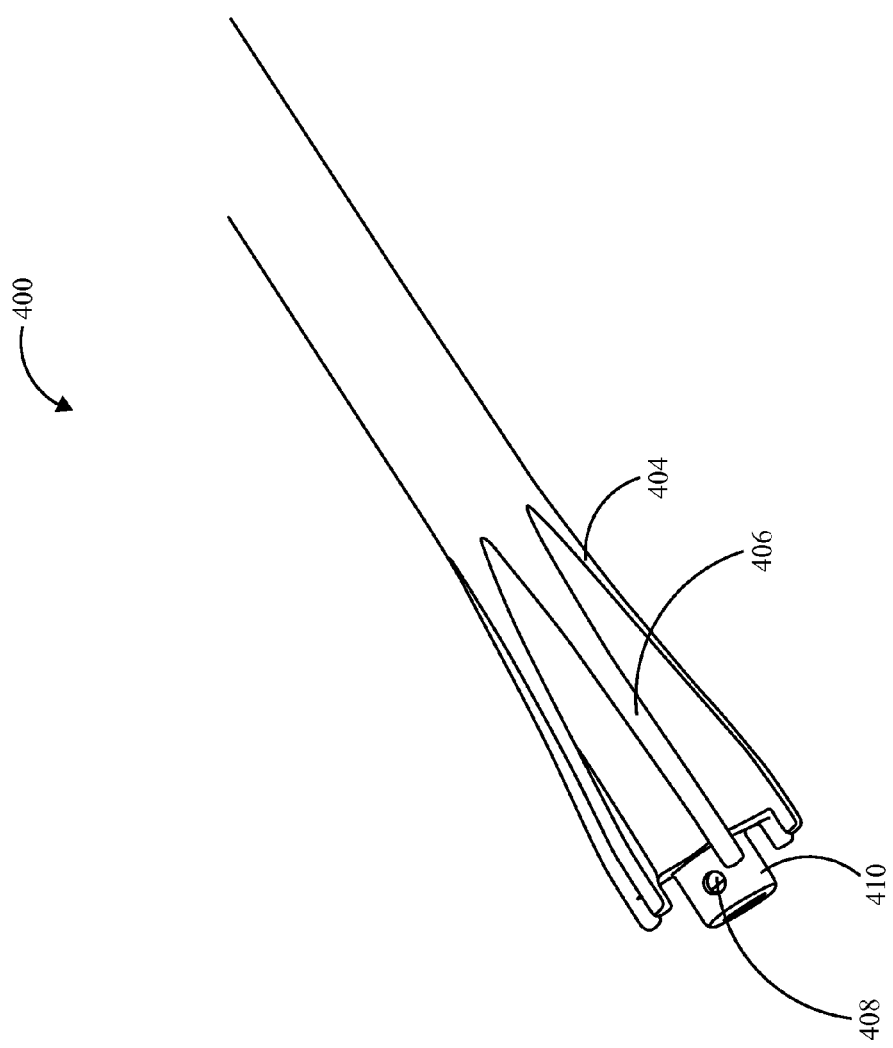
FIG. 13 is a perspective view of a plurality of prongs and radially spaced ball springs in the driver of the present invention.
Figure 14:
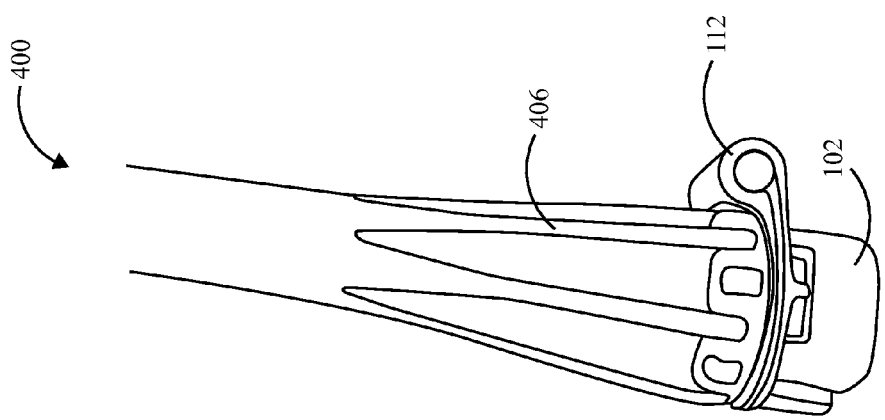
FIG. 14 is a perspective view of a cylindrical post received through a central opening in a collet head of the present invention.

FIGS. 12-14 illustrate a driver 400 configured to use with connectors. The driver 400 includes a handle connector 402 and a distal end 404. The handle connector 402 is configured to attach with detachable handles like a tear drop or T-handle. The distal end 404 is designed to connect with the collet heads 120 and 122 and drives the locking means 116, 118. As shown in FIG. 13, the distal end 404 includes a plurality of prongs 406 and a plurality of ball springs 408. The plurality of radially spaced prongs 406 is configured to engage recesses in the locking means 116 and 118 to transmit a rotational force. The plurality of ball springs 408 is radially spaced and is situated on a cylindrical post 410 extending from the center of the prongs 406. Referring to FIG. 14, the post 410 is received through a central opening 136, 138 in the collet head 120, 122. The ball springs 408 engage the cylindrical groove in the central opening 136, 138 to temporarily hold the driver 400 and the collet heads 120 and 122 together while permitting the driver 400 to rotate relative to the collet heads 120 and 122.

Figure 15:
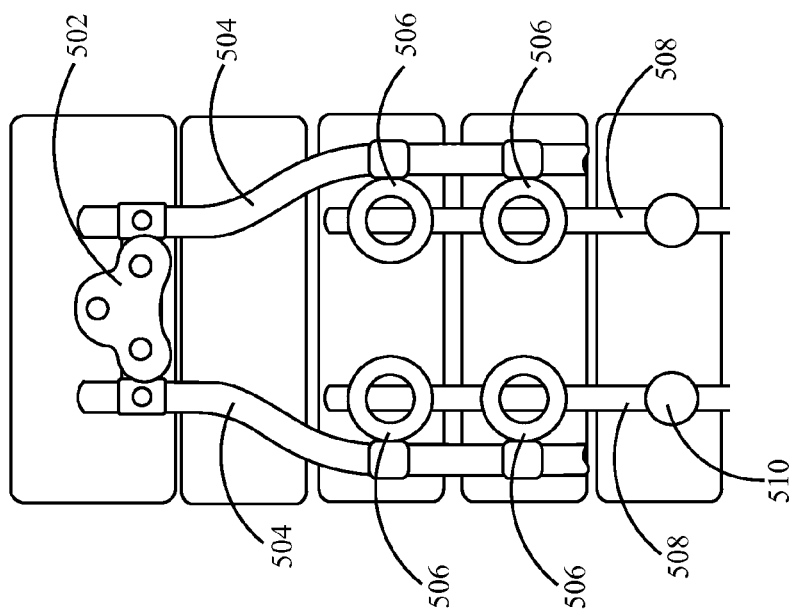
FIG. 15 is an example illustrating the usage of the connectors for connecting an occipital plate to a cervical construct.

Referring to FIG. 15, an example for the usage of the connectors 506 for connecting an occipital plate 502 to a cervical construct is illustrated. The connectors 506 are configured to use as rod connectors for linking spinal rods 124, 126 of different diameters. For example, to extend cervical and thoracic constructs to an occiput, or conversely, to a lumbar region. The connectors 506 may also be used to treat adjacent segment disease without requiring the removal of existing hardware. Additionally, the connectors 506 could be used to augment an existing construct and make it stiffer.

The spinal rods 504 may be of different diameter than the spinal rods 508. The connectors are engaged with the bone anchors 510 that connect the spinal rods 504.

Figure 16:
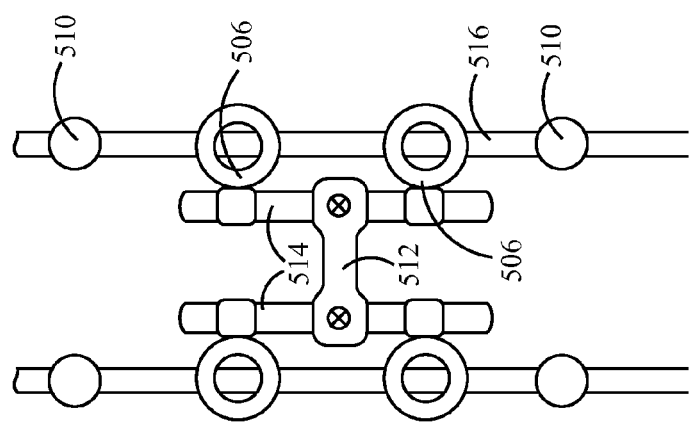
FIG. 16 is an example illustrating the usage of the connectors to augment and stiffen a spinal construct by adding supplemental spinal rods to a main spinal rod.

FIG. 16 illustrate an example illustrating the usage of the connectors 506 to augment and stiffen a spinal construct by adding supplemental spinal rods 514, to a main spinal rod 516. The supplemental spinal rods 514 may, but not necessarily, have larger (or smaller) diameters than the main rods 516. The supplemental rods 514 may be added to the construct during the initial surgery, or during a follow up procedure.

Figure 17:
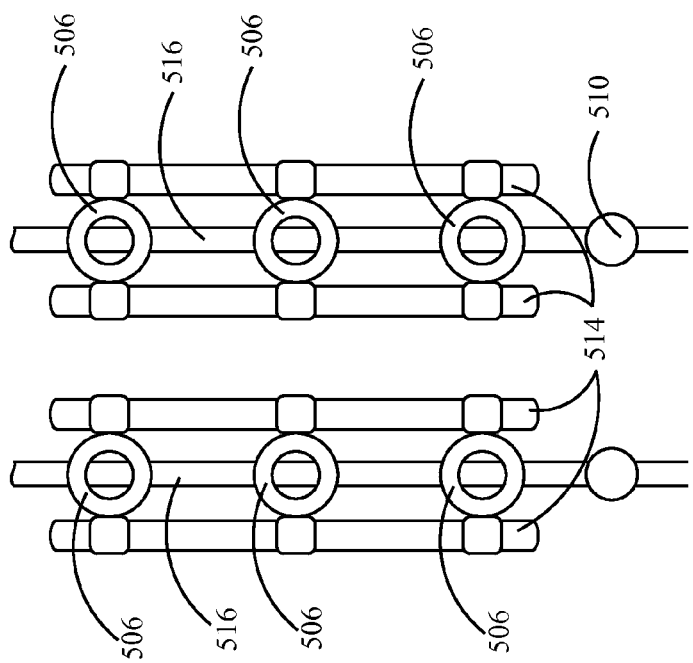
FIG. 17 is an example illustrating the usage of multiple clamps with a single connector to connect multiple elongated rods.
Figure 18:
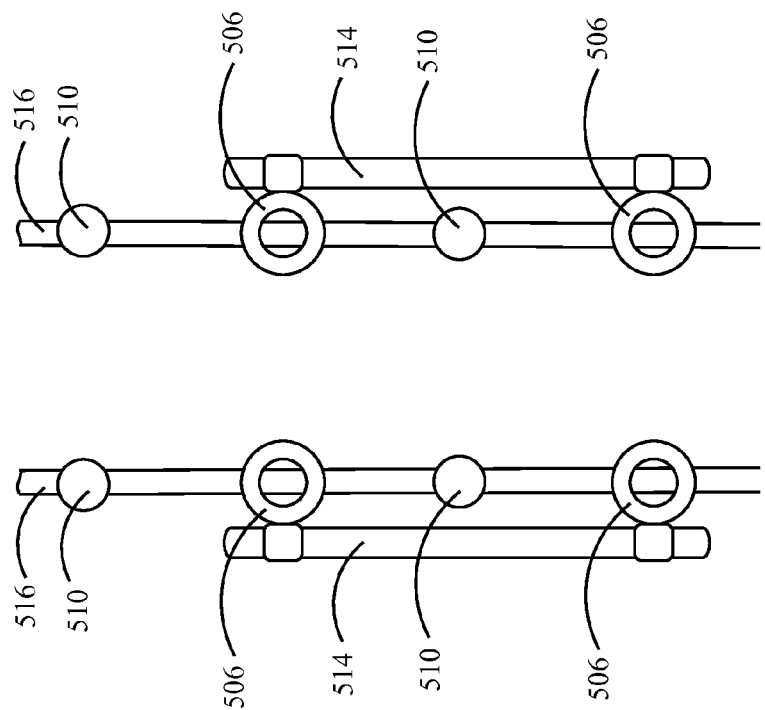
FIG. 18 is another example illustrating the usage of multiple clamps with a single connector to connect the multiple elongated rods.

FIGS. 17 and 18 are examples illustrating the usage of multiple clamps with a single connector to connect multiple elongated rods. Supplemental spinal rods 514 and connectors 506 can be used bilaterally as illustrated in FIGS. 17 and 18 or unilaterally.

Figure 19:
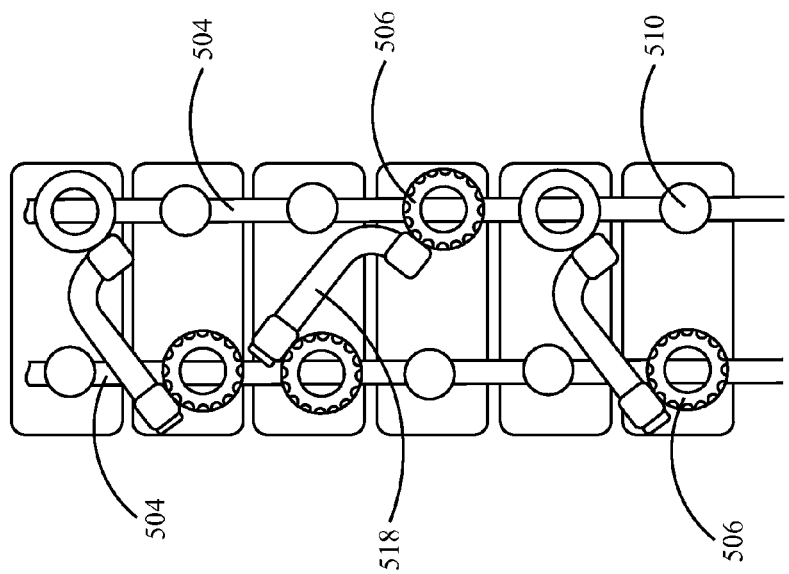
FIG. 19 is an example illustrating the usage of the connectors to augment and stiffen a spinal construct by adding a diagonal elongated member to transversely link the bilateral construct across multiple spinal segments.
Figure 20:
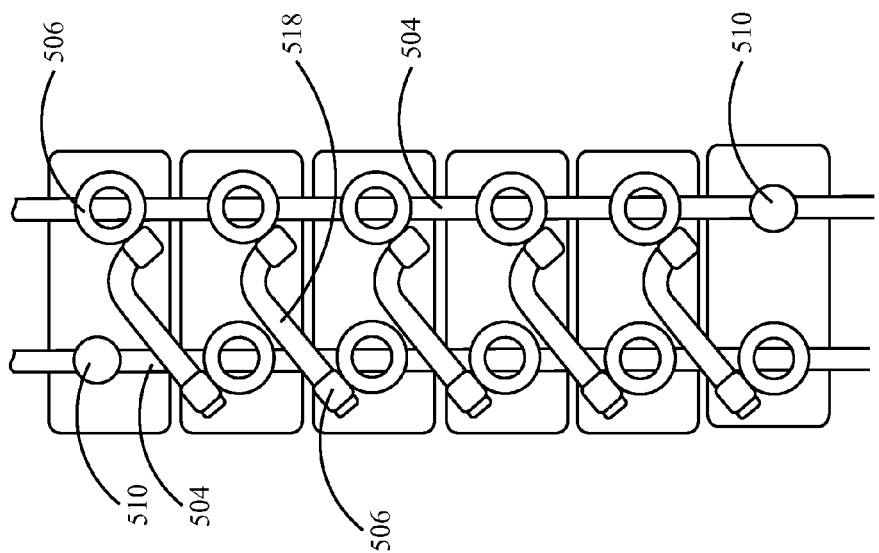
FIG. 20 shows another example illustrating the usage of the connectors to augment and stiffen the spinal construct by adding the diagonal elongated member to transversely link the bilateral construct across the multiple spinal segments.

FIGS. 19 and 20 are examples illustrating the usage of the connectors 506 to augment and stiffen a spinal construct by adding a diagonal elongated member 518 to transversely link the bilateral construct across multiple spinal segments.

Figure 21:
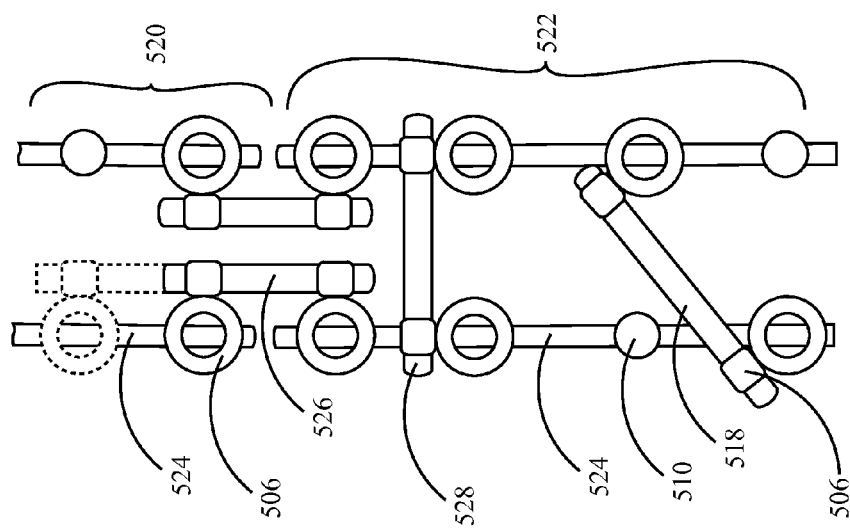
FIG. 21 shows an example where the connectors are used to connect a new spinal construct to an existing spinal construct.

FIG. 21 illustrates an example where the connectors are used to connect a new spinal construct 520 to an existing spinal construct 522, for example, during a revision surgery or during a follow on surgery to treat adjacent segment disease. With the help of the connectors the new construct 520 can be built on the adjacent level (s} without the need of removing existing hardware. The connectors are attached to the bone anchors 510 of the existing spinal construct below the adjacent level and to the new bone anchors at the adjacent level. A linking rod 526 is then connected using the clamps of the connectors.

Figure 22:
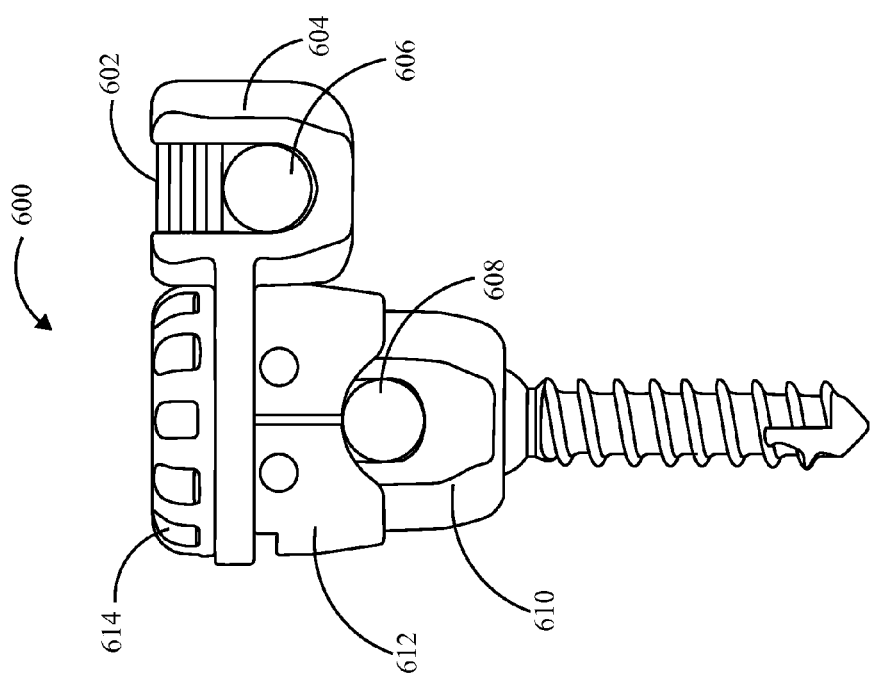
FIG. 22 shows an example of the connector with a top loading rod seat.

As shown in FIG. 22, another embodiment of the connector 600 with a top loading rod seat 604 is illustrated. Here, instead of clamps, rod seats 604 are used for receiving spinal rods 606, 608. The locking means 614 engages with the collet head 612. The collet head 612 is configured to receive the tulip 610. Set screws 602 or any closure mechanisms are used to lock the spinal rods 606, 608 in the rod seat 604.

Figure 23:
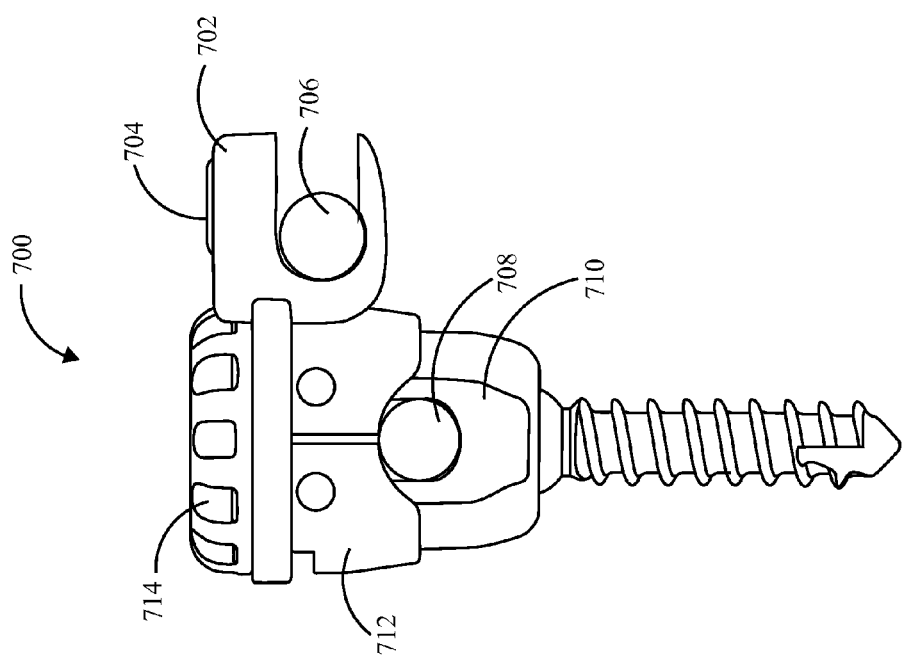
FIG. 23 shows another example of the connector with a side loading rod seat of the present invention.

FIG. 23 shows yet another embodiment of the connector 700 with a side loading rod seat 704. Here also, instead of clamps, rod seats 704 are used for receiving spinal rods 706, 708. The locking means 714 engages with the collet head 712. The collet head 712 is configured to receive the tulip 710. Set screws 702 or any closure mechanisms are used to lock the spinal rods 706, 708 in the rod seat 704. The connectors of FIGS. 22 and 23 may be used in accordance with any of the embodiments described above where multiple spinal rods are linked together.

Figure 24:
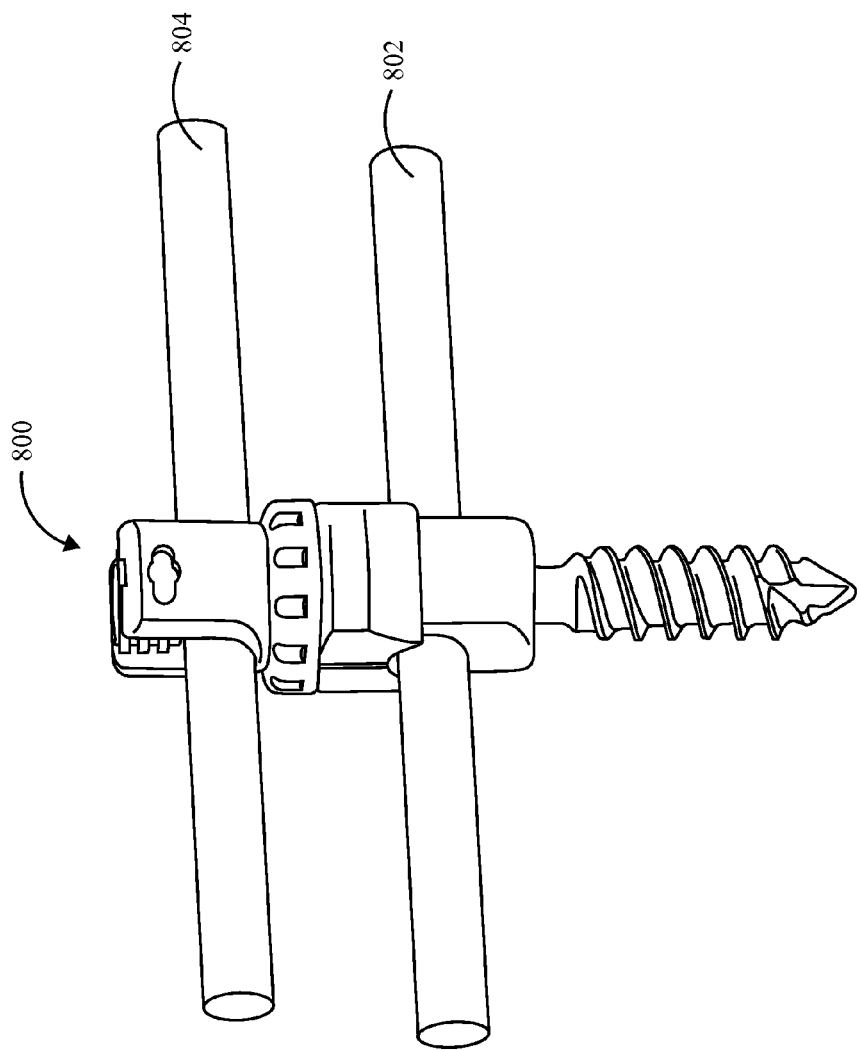
FIG. 24 shows a perspective view of a tulip head connector connected with the connector for adding multiple rods.

FIG. 24 shows a perspective view of an embodiment of a connector 506 and tulip head connector 800 to a system for adding a second rod 804. Here, a second rod 804 is collinear with a first rod 802.

Figure 25:
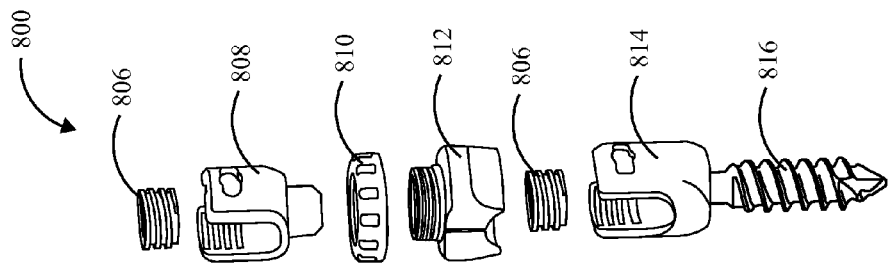
FIG. 25 shows an exploded view of the tulip head connector connected with the connector for adding multiple rods.

As shown in FIG. 25, the connector 800 and the second tulip head 808 are oriented to allow the second rod 804 to be positioned transverse to the first rod 802. The connector may be coupled to the first tulip head 814, the locking cap threaded onto the connector and the second tulip head 808 received within apertures in the connector and the locking cap 810. The second rod 804 is secured within the second tulip head 808 with the set screw 806.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention.

What is claimed is:

1. A spinal cross-connector for providing stability and rigidity to a plurality of bilateral spinal rods, comprising:
   an elongated member having a first end and a second end, said first end surrounded by a first ball spring collar having a shelled spherical shape with axial surface slits and said second end surrounded by a second ball spring collar having a shelled spherical shape with axial surface slits;
   a first connector configured to directly attach with a first pedicle screw, said first connector includes a first collet head configured to receive a first tulip head of the first pedicle screw and accommodate a first spinal rod residing within the first tulip head, a first clamp having a first spherical pocket to receive said first ball spring collar of said elongated member and permits adjustment of said elongated member relative to said first clamp, a first locking member tightened over said first collet head configured to engage with said first connector for locking said first clamp with said first end of said elongated member and locking said first connector with said first tulip; and a second connector configured to directly attach with a second pedicle screw, said second connector includes a second collet head configured to receive a second tulip head of the second pedicle screw and a plurality of cutouts to accommodate a second spinal rod residing within the second tulip head, a second clamp having a second spherical pocket to receive said second ball spring collar of said elongated member and permits adjustment of said elongated member relative to said second clamp, a second locking member tightened over said second collet head configured to engage with said second connector for locking said second clamp with said second end of said elongated member and second connector with said second tulip, said engagement of said first locking member and said second locking member with said first connector and said second connector respectively locks said spinal cross-connector.

2. The spinal cross-connector of claim 1, wherein said first ball spring collar and said second ball spring collar attached on said elongated member allows rotational adjustment to said first and second connectors in an axial plane, said rotational adjustment provides stability to said spinal cross-connector when said first tulip is positioned deeper than said second tulip on a vertebra.

3. The spinal cross-connector of claim 1, wherein said elongated member is configured to translate through said first ball spring collar and said second ball spring collar to adjust to the distance between said first spinal rod and said second spinal rod.

4. The spinal cross-connector of claim 1, wherein said first ball spring collar and said second ball spring collar are configured to rotate in said first spherical pocket and said second spherical pocket respectively to allow an axial adjustment.

5. The spinal cross-connector of claim 1, wherein said first collet head includes a recess to receive said first tulip and a plurality of cutouts to accommodate said first spinal rod.

6. The spinal cross-connector of claim 1, wherein said second collet head includes a recess to receive said second tulip and a plurality of cutouts to accommodate said second spinal rod.

7. The spinal cross-connector of claim 1, wherein said elongated member translates through said first and second spherical pockets through a conical passage.

8. The spinal cross-connector of claim 7, wherein said conical passage is larger than the diameter of said elongated member.

9. The spinal cross-connector of claim 1, wherein locking of said spinal crossconnector provides stability to said first spinal rod and said second spinal rod.

10. The spinal cross-connector of claim 1, wherein locking of said spinal crossconnector firmly secures said first spinal rod and said second spinal rod on the vertebrae.

11. A spinal implant for providing stability and rigidity to a plurality of bilateral spinal rods, comprising:

a plurality of bone anchoring elements each having a tulip and a pedicle screw; and a spinal cross-connector, said spinal cross-connector comprising:

an elongated member having a first end and a second end, said first end surrounded by a first ball spring collar having a shelled spherical shape with axial surface slits and said second end surrounded by a second ball spring collar having a shelled spherical shape with axial surface slits;

a first connector configured to directly attach with a first pedicle screw, said first connector includes a first collet head configured to receive a first tulip of the first pedicle screw and accommodate a first spinal rod residing within said first tulip, a first clamp having a first spherical pocket to receive said first ball spring collar of said elongated member and permits adjustment of said elongated member relative to said first clamp, a first locking member tightened over said first collet head engages with said first connector for locking said first clamp with said first end of said elongated member and said first connector with said first tulip; and a second connector configured to directly attach with a second pedicle screw, said second connector includes a second collet head configured to receive a second tulip of the second pedicle screw and a plurality of cutouts to accommodate a second spinal rod residing within the second tulip, a second clamp having a second spherical pocket to receive said second ball spring collar of said elongated member and permits adjustment of said elongated member relative to said second clamp, a second locking member tightened over said second collet head configured to engage with said second connector for locking said second clamp with said second end of said elongated member and second connector with said second tulip, said engagement of said first locking member and said with second locking member with said first connector and said second connector respectively locks said spinal cross-connector.

12. The spinal implant of claim 11, wherein said first ball spring collar and said second ball spring collar attached on said elongated member allows rotational adjustment to said first and second connectors in an axial plane, said rotational adjustment provides stability to said spinal cross-connector when said first tulip is positioned deeper than said second tulip on a vertebra.

13. The spinal implant of claim 11, wherein said elongated member is configured to translate through said first ball spring collar and said second ball spring collar to adjust to the distance between said first spinal rod and said second spinal rod.

14. The spinal implant of claim 11, wherein said first ball spring collar and said second ball spring collar are configured to rotate in said first spherical pocket and said second spherical pocket respectively to allow an axial adjustment.

15. The spinal implant of claim of claim 11, wherein said first collet head includes a recess to receive said first tulip and a plurality of cutouts to accommodate said first spinal rod.

16. The spinal implant of claim of claim 11, wherein said second collet head includes a recess to receive said second tulip and a plurality of cutouts to accommodate said second spinal rod.

17. The spinal implant of claim 11, wherein said elongated member translates through said first and second spherical pockets through a conical passage.

18. The spinal implant of claim 17, wherein said conical passage is larger than the diameter of said elongated member.

19. The spinal implant of claim 11, wherein locking of said spinal cross-connector provides stability to said first spinal rod and said second spinal rod.

20. The spinal implant of claim 11, wherein locking of said spinal cross-connector firmly secures said first spinal rod and said second spinal rod on the vertebrae.

* * * * *